United States Patent [19]

Seeburg

[11] Patent Number: 4,670,393
[45] Date of Patent: Jun. 2, 1987

[54] DNA VECTORS ENCODING A NOVEL HUMAN GROWTH HORMONE-VARIANT PROTEIN

[75] Inventor: Peter H. Seeburg, San Francisco, Calif.

[73] Assignee: GENENTECH, Inc., So. San Francisco, Calif.

[21] Appl. No.: 585,076

[22] Filed: Mar. 1, 1984

Related U.S. Application Data

[62] Division of Ser. No. 360,517, Mar. 22, 1982, Pat. No. 4,446,235.

[51] Int. Cl.[4] .................. C12N 5/00; C12N 15/00; C12N 5/02; C12N 1/00; C12N 1/20; C12P 21/00; C12P 21/02; C12P 19/34; C07H 21/04

[52] U.S. Cl. .................................. 435/240; 435/68; 435/70; 435/91; 435/172.3; 435/241; 435/243; 435/253; 536/27; 935/13; 935/29; 935/31; 935/32; 935/66

[58] Field of Search .................. 435/68, 70, 91, 172.3, 435/240, 241, 243, 253, 317; 935/66, 67, 68, 69, 70, 71, 72, 73, 74, 75, 11, 13, 29; 536/27

[56] References Cited

PUBLICATIONS

Lewin Gene Expression, vol. 2, Eucaryotic Chromosomes, 1974, John Wiley & Sons Ltd, London, pp. 148–153.

Ross et al, "The Human Growth Hormone Gene Family", Chem. Abstr. 98: 177038g (1983) of Horm. Drugs. Proc. FDA–USP Workshop Drug Ref. Stand. Insulins, Somatotropins, Thyroid–Axis Horm. (1982) pp. 313–318.

Pavlakis et al, "Expression of Two Human Growth Hormone Genes in Monkey Cells Infected by Simian Virus 40 Recombinants", Proc. Natl. Acad. Sci. USA 78: 7398 (1981).

*Primary Examiner*—James Martinell

[57] ABSTRACT

A novel non-allelic human growth hormone variant encoding gene is isolated using recombinant DNA techniques. The human growth hormone variant gene or a human growth hormone variant gene fused to a presequence may be inserted into cloning or expression vehicles which in turn may be used to transform cells in culture.

5 Claims, 5 Drawing Figures

```
                                      -20                                                                                        -1
              Met Ala Ala Gly Ser Arg Thr Ser Leu Leu Leu Ala Phe Gly Leu Leu Cys Leu Ser Trp Leu Gln Glu Gly Ser Ala
              ATG GCT GCA GGC TCC CGG ACG TCC CTG CTC CTG GCT TTT GGC CTG CTC TGC CTG TCC TGG CTT CAA GAG GGC AGT GCC
                           A                                                                 C
                           Thr                                                               Pro
         1                                       9                                                     20
         Phe Pro Thr Ile Pro Leu Ser Arg Leu Phe Asp Asn Ala Met Leu Arg Ala Arg Leu Tyr Gln Leu Ala Tyr Asp Thr Tyr Gln Glu
         TTC CCA ACC ATT CCC TTA TCC AGG CTT TTT GAC AAC GCT ATG CTC CGC GCC CGT CGC CTG TAC CAG CTG GCA TAT GAC ACC TAT CAG GAG
                                          (C)                                A   T   C               C   T           C
                                                                             His     His                 Phe
                                                       40                                                                    60
         Phe Glu Glu Ala Tyr Ile Leu Lys Glu Gln Lys Tyr Ser Phe Leu Gln Asn Pro Gln Thr Ser Leu Cys Phe Ser Glu Ser Ile Pro Thr
         TTT GAA GAA GCC TAT ATC CTG AAG GAG CAG AAG TAT TCA TTC CTG CAG AAC CCC CAG ACC TCC CTC TGC TTC TCA GAG TCT ATT CCA ACA
                                           CA     A                                                                  T                     G
                                           Pro
                                                                    80
         Pro Ser Asn Arg Val Lys Thr Gln Gln Lys Ser Asn Leu Glu Leu Leu Arg Ile Ser Leu Leu Leu Ile Gln Ser Trp Leu Glu Pro Val
         CCT TCC AAC AGG GTG AAA ACG CAG CAG AAA TCT AAC CTA GAG CTG CTC CGC ATC TCC CTG CTG CTC ATC CAG TCA TGG CTG GAG CCC GTG
         C              A G     A A           C                                                                            G
                        Glu Glu
                                     100                                                                                               120
         Gln Leu Leu Arg Ser Val Phe Ala Asn Ser Leu Val Tyr Gly Ala Ser Asp Ser Asn Val Tyr Arg His Leu Lys Asp Leu Glu Glu Gly
         CAG CTC CTC AGG AGC GTC TTC GCC AAC AGC CTG GTG TAT GGC GCC TCG GAC AGC AAC GTC TAT CGC CAC CTG AAG GAC CTA GAG GAA GGC
             T                                                          C         T                         GA   T   A
             Phe                                                                                             Asp Leu
                                                                                         140
         Ile Gln Thr Leu Met Trp Arg Leu Glu Asp Gly Ser Pro Arg Thr Gly Gln Ile Phe Asn Gln Ser Tyr Ser Lys Phe Asp Thr Lys Ser
         ATC CAA ACG CTG ATG TGG AGG CTG GAA GAT GGC AGC CCC CGG ACT GGG CAG ATC TTC AAT CAG TCC TAC AGC AAG TTT GAC ACA AAA TCG
                          G                                                                    G   A                C          C   A
                          Gly                                                                  Lys Thr                         Asn
                                                160                                                                                    180
         His Asn Asp Asp Ala Leu Leu Lys Asn Tyr Gly Leu Leu Tyr Cys Phe Arg Lys Asp Met Asp Lys Val Glu Thr Phe Leu Arg Ile Val
         CAC AAC GAT GAC GCA CTC CTC AAG AAC TAC GGG CTG CTC TAC TGC TTC AGG AAG GAC ATG GAC AAG GTC GAG ACA TTC CTG CGC ATC GTG
                                   A

191
         Gln Cys Arg Ser Val Glu Gly Ser Cys Gly Phe
         CAG TGC CGC TCT GTG GAG GGC AGC TGT GGC TTC
```

```
                5'-NONTRANSCRIBED

-497                                                                                            -400
HGH-N    GAATTCAGGACTGAATCGTGCTCACAACCCCCACAATCTATTGGCTGTGCTT-GGCCCCTTTTCCCAACACACACATTCTGTCTGGTGGGTGGAGGTTAAACATGCGGGGA
HGH-V    GAATTCAGCACTGAATCATGCCCAGAACCCCCGCAATCTATTGGCTGTGCTTTGGCCCCTTTTCCCAACACACACATTCTGTCTGGTGGGTGGAGGGGAAACATGCGGGGA
HCS      GAATTCAGGACTCAATGGTGCTCAGAACCCCCACAATCTATTGGCTGTGCTT-GGCCCCTTTTCCCAACACACACATTCTGTCTGGTGGGTGGAAGTTAAACACGCGGGGA

-350                                                               -300
HGH-N    GGAGGAAAGGGATAGGATAGAGAATGGGATGTGGTCGGTAGGGGGTCTCAAGGACTGGCCTATCCTGACATCCTTCGCCCGCGTGCAGGTTGGCCACCATGGCCTGCGGCC
HGH-V    GGAGGAAAGGAATAGGATAGAGAGTGGGATGGGGTCGGTAGGGG-TCTCAAGGACTGGCCTATCCTGACATCCTTCTCC-GCGTTCAGGTTGGCCACCATGGCCTGCTGCC
HCS      GGAGGAAAGGAATAGGATAGAGAGTGGAATGGGGTCGGTAGGGG-TCTCAAGGACTGGC-TATCCTGACAGCCTTCCCC-GCGTTCAGGTTGACCAACATGGCCTGCAGCC

-250                                                               -200
HGH-N    AGAGGGCACCCACGTGACCCTTAAAGAGAGGACAAGTTGGGTGGTATCTCTGGCTGACACTCTGTGCACAACCCTCACAACACTGGTGACGGTGGGAAGGGAAAGATGACA
HGH-V    AGAGGGCACCCACGTGACCCTTAAAGAGAGGACAAGTTGGGTGGTATCTCTGGCTGACATTCTGTGCACAACCCTCACAACGCTGGTGATGGTGGGAAGGGAAAGATGACA
HCS      AGAGGGCACCCACCTGACCCTCAAAGAGAGGACAAGTTGGGTGGAGTCTGTGGCTGACACTCTGTGCACAATCCTTACAACATCGGTGATGGTGAGAAGGGAAAGACGACA

-150                                                               -100
HGH-N    AGCCAGGGGGCATGATCCCAGCATGTGTGGGAGGAGCTTCTAAATTATCCATTAGCACAAGCCCGTCAGTGGCCCCATGCATAAATGTAGCACAGAAACAGGTGGGGTCAA
HGH-V    AGTCAGGGGGCATGATCCCAGCATGTGTGGGAGGAGCTTCTAAATTATCCATTAGCACAAGCCCGTCAGTGGCCCCAGGCCTAAACAT-GCAGAGAAACAGGTGAGGAGAA
HCS      AGCCAGGGGGCATGATCCCAGCATGTGTGGGAGGAGCTTCCAAATTATCCATTAGCACAAGCCCGTCAGTGGCCCCATGCATAAATGTA-CACAGAAACAGGTGGGGTCAA

-30                           -1
HGH-N    -CAGTGGGAGAGAA---GGGGCCAGGGTATAAAAAGGGCCCACAAGAGACCAGCTCA
HGH-V    GCAGCGAGAGAGAA---GGGGCCAGG-TATAAAAAGGGCCCACAAGAGACCAGCTCA
HCS      GCAGGGAGAGAGAACT-GGGCCAGGGTATAAAAAGGGCCCACAAGAGACCGGCTCT

EXON I
                                                          60
HGH-N    AGGATCCCAAGGCCCAACTCCCCGAACCACTCAGGGTCCTGTGGACAGCTCACCTAGCTGCA      ATG GCT ACA G
HGH-V    AGGATCCCAAGGCCCAACTCCCCGAACCACTCAGGGTCCTGTGGACAGCTCAC-TAGCGGCA      ATG GCT GCA G
HCS      AGGATCCCAAGGCCCAACTCCCCGAACCACTCAGGGTCCTGTGGACAGCTCACCTAGTGGCA      ATG GCT GCA G
                                                                                       -25

INTRON A
                                 100
HGH-N    GTAAGCGCCCCTAAAATCCCTTTGGCACAATGTGTCCTGAGGGGAGAGGCAGCGACCTGTAGATGGGACGGGGGCACTAACCCTCAGGGTTTGGGG-TTCTGAATGTGAG-
HGH-V    GTAAGCGCCCCTAAAATCCCTTTGGCACAATGTGTCCTGAGGGGAGAGGCGGCGTCCTGTAGATGGGACGGGGGCACTAACCCTCAGG-TTTGGGGCTTATGAATGTTAGC
HCS      GTAAGCGCCCCTAAAATCCCTTTGGCACAACGTGTCCTGAGGGGAGAGGCAGCGCCCTGTAGATGGGACGGGGGCACTAACCCTCAGG-TTTGGGGCTTATGAATGTGAG-

200
HGH-N    TATCGCCATGTAAGCCCAG-TATTTGGCCAATCTCAGAAAGCTCCTGGCTCCCTGGAGG-ATGG----------AGAGAGAAAACAAA---CAGCTCCTGGAGCAGGGA
HGH-V    TATCGCCATCTAAGCCCAG-TATTTGGCCAATCTCTGAATGTTCCTGG-TCCCTGGAGG-A-GGCAGAGAGAGAGAGAGAAAAAAAAACCCAGCTCCTGGAACAGGGA
HCS      TATCGCCATCTAAGGCCAGATATTTGGCCAATCTCTGAATGTTCCTGG-TCTCTGGAGGGATGG-------AGAGAGAAAAAAACAAA---CAGCTCCTGGAGCAGGGA

300
HGH-N    GAGTGTTGGCCTCTTGCTCTCCGGCTCCCTCTGTTGCCCTCTGGTTTCTCCCCAG
HGH-V    GAGCGCTGGCCTCTTGCTCTCCAGCTCCCTCTGTTGCC-TCCGGTTTCTCCCCAG
HCS      GAGCGCTGGCCTCTTCCTCTCCGGCTCCCTCCATTGCC-TCCGGTTTCTCCCCAG

EXON II
                                                                                                                 400
HGH-N    GC TCC CGG ACG TCC CTG CTC CTG GCT TTT GGC CTG CTC TGC CTG CCC TGG CTT CAA GAG GGC AGT GCC TTC CCA ACC ATT CCC
HGH-V    GC TCC CGG ACG TCC CTG CTC CTG GCT TTT GGC CTG CTC TGC CTG TCC TGG CTT CAA GAG GGC AGT GCC TTC CCA ACC ATT CCC
HCS      GC TCC CGG ACG TCC CTG CTC CTG GCT TTT GCC CTG CTC TGC CTG CCC TGG CTT CAA GAG GCT GGT GCC GTC CAA ACC GTT CCG
                   -20                                                                                 -1    1

HGH-N    TTA TCC AGG CTT TTT GAC AAC GCT ATG CTC CGC GCC CAT CGT CTG CAC CAG CTG GCC TTT GAC ACC TAC CAG GAG TTT
HGH-V    TTA TCC AGG CTT TTT GAC AAC GCT ATG CTC CGC GCC CGT CGC CTG TAC CAG CTG GCA TAT GAC ACC TAT CAG GAG TTT
HCS      TTA TCC AGG CTT TTT GAC CAC GCT ATG CTC CAA GCC CAT CGC GAC CAC CAG CTG GCC ATT GAC ACC TAC CAG GAG TTT
                                                                     20

INTRON B
                  500                                                                                              600
HGH-N    GTAAGCTCTTGGGGAATGGGTGCGCATCAGGGGTGGCAGGAAGGGGTGACTTTCCCCCGCTGGAAA-TAAGAGGAGGAGACTAAGGAGCTCAGGGTTTTTCCCGACCGCGA
HGH-V    GTAAGCTCTTGGGTAATGGGTGCGCTTCAGAGGTGGCAGGAAGGGGTGAATTTCCCCCGCTGGGAAGTAATGGGAGGAGACTAAGGAGCTCAGGGTTGTTTTCTGAAGTGA
HCS      GTAAGTTCTTGGGGAATGGGTGCGGGTCAGGGGTGGCAAGAAGGGGTGACTTTCCCCCACTGGAAG-TAATGGGAGGAGACTAAGGAGCTCAGGGTTGTTTTCTGAAGCGA

HGH-N    AAATGCAGGCAGATGAGCACACGCTGAGCTAGGTTCCCAGAAAAGTAA-AATGGGAGCAGGTCTC-AGCTCAGA--------------CCTTGGTGGGCGGTCCTTCTCCTAG
HGH-V    AAATGCAGGCAGATGAGCATACGCTGAGTGAGGTTCCCAGAAAAGTAACAATGGGAGCAGGTCTCCAGCATAGA--------------CCTTGGTGGGCGGTCCTTCTCCTAG
HCS      AAATGCAGGCAGATGAGCATAGGCTGAGCCAGGTTCCCAGAAAAGCAACAATGGGACCTGGTCTCCAGCATAGAAACCAGCAGTCCTTCTTGGTGGGGGGTCCTTCTCCTAG

EXON III
               700
HGH-N    GAA GAA GCC TAT ATC CCA AAG GAA CAG AAG TAT TCA TTC CTG CAG AAC CCC CAG ACC TCC CTC TGT TTC TCA GAG TCT ATT CCG
HGH-V    GAA GAA GCC TAT ATC CTG AAG GAG CAG AAG TAT TCA TTC CTG CAG AAC CCC CAG ACC TCC CTC TGC TTC TCA GAG TCT ATT CCA
HCS      GAA GAA ACC TAT ATC CCA AAG GAC CAG AAG TAT TCA TTC CTG CAT GAC TCC CAG ACC TCC TTC TGC TTC TCA GAC TCT ATT CCG
                                                            40
                    800
HGH-N    ACA CCC TCC AAC AGG GAG GAA ACA CAA CAG AAA TCC
HGH-V    ACA CCT TCC AAC AGG GTG AAA ACG CAG CAG AAA TCT                                      FIG. 2a
HCS      ACA CCC TCC AAC ATG GAG GAA ACG CAA CAG AAA TCC
             60

INTRON C
                                                                                                       900
HGH-N    GTGAGTGGATGCCTTCTCCCCAGGCGGGGATGGGGGAGACCTGTAGTCAGAGCCCCGGGCAGCACAGCCAATGCCCGTCCTTGCCCCTGCAG
HGH-V    GTGAGTGGATGCCTTCTCCCCAGGTGGG-ATGGGGTAGACCTGTGGTCAGAGCCCCGGGCAGCACAGCCACTGCCGGTCCTT-CCCCTGCAG
HCS      GTGAGTGGATTCCGTCTCCCTAGGCGGGGATGGGGGAGACCTGTGGTCAGGGCTCCCGGGCAGCACAGCCACTGCCGGTCCTT-CCCCTGCAG
```

EXON IV

```
HGH-N  AAC CTA GAG CTG CTC CGC ATC TCC CTG CTG CTC ATC CAG TCG TGG CTG GAG CCC GTG CAG TTC CTC AGG AGT GTC TTC GCC AAC
HGH-V  AAC CTA GAG CTG CTC CGC ATC TCC CTG CTG CTC ATC CAG TCA TGG CTG GAG CCC GTG CAG CTC CTC AGG AGC GTC TTC GCC AAC
HCS    AAT CTA GAG CTG CTC CGC ATC TCC CTG CTG CTC ATC GAG TCG TGG CTG GAG CCC GTG CGG TTC CTC AGG AGT ATG TTC GCC AAC
                                                80
           1000
HGH-N  AGC CTG GTG TAC GGC GCC TCT GAC AGC AAC GTC TAT GAC CTC CTA AAG GAC CTA GAG GAA GGC ATC CAA ACG CTG ATG GGG
HGH-V  AGC CTG GTG TAT GGC GCC TCG GAC AGC AAC GTC TAT GCC CAC CTG AAG GAC CTA GAG GAA GGC ATC CAA ACG CTG ATG TGG
HCS    AAC CTG GTG TAT GAC ACC TCG GAC AGC GAT GAC TAT CAC CTC CTA AAG GAC CTA GAG GAA GGC ATC CAA ACG CTG ATG GGG
           100.                                                                                  120
```

INTRON D

```
                      1100
HGH-N  GTGAGGGTGGCGCCAGGGGTCCCCAATCCTGGAGCCCCACTGACTTTGAGA-GACTGTGTTAGAGAAACACTGGCTGCCCTCTTTTTAGCAGTCAGGCCCTGACCCAAGAG
HGH-V  GTGAGGGTGGCACCAGGA-TCC--AATCCTGGGGCCCCACTGGCTTCCAGG-GACT-GGGGAGAGAAACACTG-CTGCCCTCTTTTTAGCAGTCAGGCGCTGACCCAAGAG
HCS    GTGAGGGTGGCGCCAGGGGTCCGCAATCCTGGAACCCCACTGGCTT--AGAGGGCTGGGGGAGAGAAACACTG-CTGCCCTCTTTGTAGCAGTCAGGCGCTGACCCAAGAG
             1200
HGH-N  AACTCACCTTATTCTTCATTTCCCCTCGTGAATCCTCCAGGCCTTTCTCTACA--CTGAAGGGGAGGGAGGAAAATGAATGAATGAGAAAGGGAGGGAACAGTACCCAAGC
HGH-V  AACTCACCGTATTCTTCATTTCCCCTCGTGAATCCTCCAGGCCTTTCTCTACAACCTGGAGGGGAGGGAGGAAAATGGATGAATGAGAGAGGGGGGAACAGTGCCCAAGC
HCS    AACTCACCTTATTCTTCATTTGGCCTGGT-AATCCTCCAGGCCCTTCTCTACACCCTGAAGGGGAGGGAGGAAAATGGATGAATGAGAGAGGGGAGGGAACATTGCCCAAGC
             1300
HGH-N  GCTTGGCCTCTCCTTCTCTTCCTTCACTTTGCAG
HGH-V  GCTTGGCCTCTCCTTCTCTTCCTTCACTTTGCAG
HCS    GCTTGGCCTCTCCTTCTCTTCCTTCACTTTGCAG
```

EXON V

```
                                                                                                    1400
HGH-N  AGG CTG GAA GAT GGC AGC CCC CGG ACT GGG CAG ATC TTC AAG CAG ACC TAC AGC AAG TTC GAC ACA AAC TCA CAC AAC GAT GAC
HGH-V  AGG CTG GAA GAT GGC AGC CCC CGG ACT GGG CAG ATC TTC AAT CAG TCC TAC AGC AAG TTT GAC ACA AAA TCG CAC AAC GAT GAC
HCS    AGG CTG GAA GAT GGC AGC CGC CGG ACT GGG CAG ATC CTC AAG CAG ACC TAC AGC AAG TTT GAC ACA AAC TCA CAC AAC CAT GAC
                                                140

HGH-N  GCA CTA CTC AAG AAC TAC GGG CTG CTC TAC TGC TTC AGG AAG GAC ATG GAC AAG GTC GAG ACA TTC CTG CGC ATC GTG CAG TGC
HGH-V  GCA CTG CTC AAG AAC TAC GGG CTG CTC TAC TGC TTC AGG AAG GAC ATG GAC AAG GTC GAG ACA TTC CTG CGC ATC GTG CAG TGC
HCS    GCA CTG CTC AAG AAC TAC GGG CTG CTC TAC TGC TTC AGG AAG GAC ATG GAC AAG GTC GAG ACA TTC CTG CGC ATG GTG CAG TGC
                                                160                                                                 180
          1500
HGH-N  CGC TCT GTG GAG GGC AGC TGT GGC TTC          TAGCTGCCCGGGTGGCATCCCTGT-----GACCCCTCCCCAGTGCCTCTCCTGGCCCTGGAAGTTGCCAC
HGH-V  CGC TCT GTG GAG GGC AGC TGT GGC TTC          TAGCTGCCCGGGTGGCATCCCTGT-----GACCCCTCCCCAGTGCCTCTCCTGGTCGTGGAAGGTGCTAC
HCS    CGC TCT GTA GAG GGT AGC TGT GGC TTC          TAGGTGCCCGCGTGGCATCC-TGTGAGCCGACCCCTCCCCAGTGCCTCTCCTGGCCCTGGAAGGTGCCAC
                                                   191
           1600
HGH-N  TCCAGTGCCCACCAGCCTTGTCCTAATAAAATTAAGTTGCATC
HGH-V  TCCAGTGCCCACCAGCCTTGTCCTAATAAAATTAAGTTGCATC
HCS    TCCAGTGCCCATCAGCCTTGTCCTAATAAAATTAAGTTGTATCATTTC
```

3'-NONTRANSCRIBED

```
                                                                              1700
HGH-N  ATTTTGTCTGACTAGGTGTCC-TTCTATAATATTATGGGGTGGAGGGGGGTGGTATGGAGCAAGGGGCCCAAGTTGGGAAGACAACCTGTAGGGCCTGCGGGGTCTATTCG
HGH-V  ATTTTGTTTGACTAGGTGTCC--TTGTATAATATTATGGGGTGGAGGCGGGTGGTATGGAGCAAGGGG-CCAGGTTGGGAAGACAACCTGTAGGGCCTTCAGGGTCTATTCG
HCS      ATCTGACTAGGTGTCGATTCTATAATATTATGGGGTGGAAGGTGGTGGTATGGAGCAAGGGG--TAGGT-GGAAAGAAGACCTGGAGGGCCTTGAAGATCTATT-G
                                                              1800
HGH-N  GGAACCAAGCTGGAGTGCAGTGGCACAATCTTGGCTCACTGCAATCTCCGCCTCCTGGGTTCAAGCGATTCTCCTGCCTCAGCCTCCCGAGTTGTTGGGATTCCAGGCATG
HGH-V  GGAACCAGGCTGGAGTGCAGTGGCA---GTCTTGGCTCGCTGCAATCTCCGCCTCCTGGGTTCAAGCGATTCTCCTGCCTCAGTCTCCCGAATAGTTGGGATTCAGGCATG
HCS    GGAACTAGGCTGAAATATAA------GAGGCTTGGCT-GTTCCTGGGCCAGAAAAAGGCTGACACATCACCGCTATTACTCACTAAGGCCATTCACCAGCTCAGTGGTCCCA
                                                1900
HGH-N  CATGACCAGGCTCAGCTAATTTTTGTTTTTTTGGTAGAGACGGGGTTTCACCATATTGGCCAGGCTGGTCTCCAACTCCTAATCTCAGGTGATCTACCCACCTTGGCCTCC
HGH-V  CAAGACCAGGCTCAGCTAATTTTTGTATTTTTGGTAGAGACGGGGTTTCACCATATTGGCCAGTCTGGTCTCCATCTCCTGACCTCAGGTAATCCGCCCGCCTCGGCCTCC
HCS    GCTTGCTGTCACAGCTCATTGGTCATCCCAGAGATGACTTGAAGGCATTTCTTCCTCCCCCACCATCACCAGCAACACCAAACCTAGCCCTCCAGGAGCCGGCGAAGAAAT
                                      2000
HGH-N  CAAATTGCTGGGATTACAGGCGTGAACCACTGCTCCCTTCCCTGTCCTTCTGATTTTAAAATAACTATACCAGCAGGAGGACGTCCAGACACAGCATAGGCTACCTG-CCA
HGH-V  CAAATTGCTGGGATTACAGGTATGAGCCACTGGGCCTTCCCTGTCCT-GTGATTTTAAAATAATTATACCAGCAGAAGGACGTCCAGACACAGCATGGGCTACCTGGCCA
HCS    GAAAACAAGATGGGCTATTAAGTGCAGAGACAAAAAGCCTCCCCAACAGGTGAGGAAACAATGGCCATAGAATTACTTGTGTTCAGAAGAATTTTAGGATGAATATTCCTT
           2100
HGH-N  TGGCCCAACCGGTGGGACATTTGAGTTGCTTGCTTGGCACTGTCCTCTCATGCGTTGGGTCCACTCAGTAGATGCCTGTTGAATTC
HGH-V  TG-CCCAGCCAGTTGGACATTTGAGTTGTTTGCTTGGCACTGTCCTCTCATGCATTGGGTCCACTCAGTAGATGCTTGTTGAATTC
HCS    AAGCCCAACTACTCTCGGGAAATGAGATCCAATGTCAAAAATGAGTTTGAGACATACAGAACCAGAGCATTTGGAATCTGAATTAGGGCAAGGGAAGTGGAAGAGAGATTT
              2200                                                                                            2300
HCS    TATTTGGGGTTGTAAATGCATGCCAACAGTGCCAGGTAGATAACGAACGTAAGCAATCGAGGGCTGGATGGGAGGGGATAAATCCCGAGATGACACTCGCTTGTCCTTCAG
                                                                                                                2400
HCS    GGGATGCAACACAGAGGGGTGGGAACCAGCACAATCTGCAGAACTCAAGCCCCTGCTGAGTGGGACCCACCCAGCCTGTCACCATCAGGACTGAAGGGACACGGCTTCCAG

HCS    ACCTTCTGATTCTTTGAGACAGCCAGGACATCCAGACTTTTACGAGGAATTC
```

DNA VECTORS ENCODING A NOVEL HUMAN GROWTH HORMONE-VARIANT PROTEIN

This application is a division of application Ser. No. 360,517, filed Mar. 22, 1982, now U.S. Pat. No. 4,446,235.

FIELD OF THE INVENTION

The present invention is based upon the discovery of variant proteins of human growth hormone and to the determination of the DNA sequence and deduced amino acid sequence thereof via recombinant DNA technology. It further provides the means and methods for producing useful amounts of such variant proteins by expression of DNA in host microorganism or cell culture.

BACKGROUND OF THE INVENTION

Means and methods for the microbial production of numerous polypeptides, including human growth hormone, were disclosed by Goeddel et al. in U.S. Ser. No. 55126, filed July 5, 1979, which is hereby incorporated by reference. Counterparts of the application have been published, e.g. British patent application publication no. 2055382 and European patent application publication no. 22242.

Methods for producing various heterologous polypeptides from microorganism hosts have required the identification of the DNA sequence encoding the particular desired product. Once known, the sequence could be fashioned, syntnetically or from tissue derived cDNA, and operably inserted into expression vectors that were then used to transform the host organism and thus direct its production of the polypeptide. In the past, relatively small proteins could be produced by synthesizing the entire gene. The first example of this was human insulin (see British patent application publication no. 2007676, for example). For polypeptides too large to admit of microbial expression from entirely synthetic genes, cDND was obtained from mRNA transcripts derived from tissue.

In each case, knowledge of the sequence of the amino acid was essential so that the correct sequential synthesis was conducted in the one case and that correct homologous sequence probes for isolating appropriate mRNA sequences could be used in the other.

Problems are encountered where the sequence of the polypeptide is unknown and the source of the polypeptide contains insufficient amounts to insure extraction of enough material for sequencing. Thus, hitherto employed methods fail where the gene is expressed in unknown tissue or in undetectable amounts or in very few cells of a tissue or because of other reasons related to limitations imposed by the current state of the art concerning the isolation of rare mRNA.

It was perceived that improved refinements in recombinant DNA techniques would be useful in providing desired heterologous protein under such circumstances.

SUMMARY OF THE INVENTION

The present invention is based upon the discovery that recombinant DNA technology can be used to advantage in isolating genes in sufficient amounts to permit sequencing where in the native state the products of such genes are either not produced in identifiable amounts or in amounts insufficient to permit their useful isolation.

This invention provides a process involving probing the native gene bank, derived from genomic DNA, to obtain genomic sections containing the desired gene together with any naturally occurring intron sequences associated with it. These sections are incorporated into host cells such that transcription faithfully produces corresponding mRNA transcripts. Such transcripts are devoid of sequence(s) corresponding to any intron sequence that may have been present in the original gene, being spliced out as part of the post-transcription processes. From the mRNA transcripts, a cDNA bank is prepared from which the cDNA encoding the desired protein product is isolated and thereafter operably inserted into an expression vector via procedures known per se. Unique is the method of producing desired mRNA, and thence cDNA, for expression vector use, from total genomic DNA, without the benefit of hindsight application of DNA sequence knowledge.

This is a method of general application by which mRNA, and thence cDNA, can be obtained from a portion of chromosomal DNA containing a gene of human, mammalian, or other eucaryotic origin. The method is useful in those cases where the gene, but not the mRNA derived from this gene, can be isolated. This occurs because the product of gene expression is not detectable, for reasons set forth supra. A small segment of chromosomal DNA carrying the desired gene can be isolated from a genomic library employing a suitable DNA hybridization probe. This DNA is then introduced into the nuclei of suitable tissue culture cells by means of any one of a number of existing techniques that guarantee the efficient expression of the gene. The gene is transcribed, the primary transcription product processed by removal of intron sequences, capping and polyadenylation and the final transcription product, the mRNA, appears in the cellular cytoplasm as a template for protein synthesis. Thus, a cDNA bank derived from the polyadenylated mRNA from such cells will contain cloned cDNA derived from the gene of interest and this cDNA can then be processed for bacterial expression by standard procedures.

Several methods are currently known for the introduction of foreign genes into the nuclei of cells (microinjection, cotransformation using genetic markers and eucaryotic vectors derived from the genomes of animal viruses). Only a few result in the efficient expression of introduced genes. One system with such properties is the COS cell which carries the SV40 T antigen gene in its chromosomes such that DNA containing the SV40 origin of replication introduced into the cells will replicate in high copy number. Efficient expression of DNA physically linked to this origin is made possible by utilizing the SV40 late promoter function.

This aspect of the present invention can be illustrated by a particular scheme as follows:

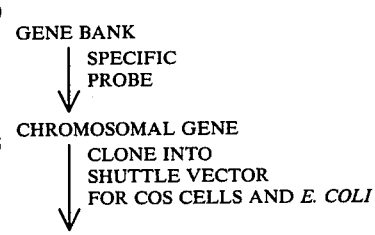

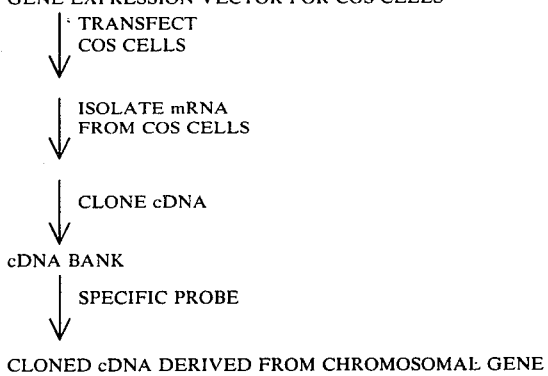

```
-continued
GENE EXPRESSION VECTOR FOR COS CELLS
        │ TRANSFECT
        │ COS CELLS
        ▼

│ ISOLATE mRNA
        │ FROM COS CELLS
        ▼

│ CLONE cDNA
        ▼
cDNA BANK
        │ SPECIFIC PROBE
        ▼
CLONED cDNA DERIVED FROM CHROMOSOMAL GENE
```

The present invention is further based upon the discovery of variants of human growth hormone. In particular, a representative gene coding for an HGH variant protein and containing four intervening sequences has been isolated from a human genomic library. No tissue is known which produces this protein; in fact, the existence of the HGH variant (HGH-V) protein has never been described. To produce the protein by recombinant DNA technology it is essential to obtain a cloned cDNA copy of the mRNA of this gene. Using the method described above, a tissue culture system is employed to produce the desired mRNA (for starting material for cDNA synthesis). The gene is cloned into a bacterial vector (plasmid pML) containing the SV40 origin of replication and late promoter function. In this construct, the HGH-V gene is linked to the SV40 promoter to ensure transcription of the correct strand. After obtaining sufficient amounts from a bacterial culture this DNA is used to transfect COS cells. The expression of the HGH-V gene is monitored in transfected cells by RNA analysis and RIA. Approximately five days after infection cells are harvested, RNA is extracted and polyadenylated RNA is prepared. Double-stranded cDNA is synthesized and a cloned bank of transfected COS cell cDNA is established by standard procedures. This bank is probed with an appropriate nuclei acid probe to detect colonies carrying cloned cDNA derived from HGH variant mRNA. DNA sequence analysis is used to determine whether the cloned HGH-V cDNA is devoid of intron sequences indicating correct splicing of the primary gene transcript in COS cells. Standard technology is used to construct a bacterial expression vector for the HGH variant protein starting with the cloned cDNA.

This invention is directed to method of isolating mRNA and to HGH variant in all of their respective aspects, and is not to be construed as limited to any specific details described herein embraced within the general compass of this invention.

Being variants of human growth hormone (HGH), that is known to be useful, inter alia, for the treatment of hypopituitary dwarfism, the products hereof are doubtless implicated in the general anabolic and other metabolic activities of the processes involving HGH itself. Thus, they would be useful in evoking activities within the sphere of general anabolic and other metabolic activities ascribed to HGH and may prove to have divergent activities outside of an overlapping set common with HGH.

DESCRIPTION OF PREFERRED EMBODIMENTS

A. Microorganisms/Cell Cultures

1. Bacterials Strains/Promoters

The work described herein was performed employing the microorganism E. coli K-12 strain 294 (end A, thi−, hsr−, $_k$hsm+). This strain has been deposited with the American Type Culture Collection, ATCC Accession No. 31446. However, various other microbial strains are useful, including known E. coli strains such as E. coli B, E. coli X 1776 (ATCC No. 31537) or other microbial strains many of which are deposited and (potentially) available from recognized microorganism depository institutions, such as the American Type Culture Collection (ATCC)—cf. the ATCC catalogue listing. These other microorganisms include, for example, Bacilli such as Bacillus subtilis and other enterobacteriaceae among which can be mentioned as examples Salmonella typhimurium and Serratia marcesans, utilizing plasmids that can replicate and express heterologous gene sequences therein.

As examples, the beta lactamase and lactose promoter systems have been advantageously used to initiate and sustain microbial production of heterologous polypeptides. More recently, a system based upon the tryptophan operon, the so-called trp promoter system, has been developed. Numerous other microbial promoters have been discovered and utilized and details concerning their nucleotide sequences, enabling a skilled worker to ligate them functionally within plasmid vectors, are known.

2. Yeast Strains/Yeast Promoters

The expression system hereof may also employ a plasmid which is capable of selection and replication in both E. coli and the yeast, Saccharomyces cerevisiae. One useful strain is strain RH218 deposited at the American Type Culture Collection without restriction (ATCC No. 44076). However, it will be understood that any Saccharomyces cerevisiae strain can be employed.

When placed on the 5′ side of a non-yeast gene the 5′-flanking DNA sequence (promoter) from a yeast gene can promote the expression of a foreign gene in yeast when placed in a plasmid used to transform yeast. Besides, a promoter, proper expression of a non-yeast gene in yeast requires a second yeast sequence placed at the 3′-end of the non-yeast gene on the plasmid so as to allow for proper transcription termination and polyadenylation in yeast. This promoter can be suitably employed in the present invention as well as others—see infra.

Because yeast 5′-flanking sequence (in conjunction with 3′ yeast termination DNA) (infra) can function to promote expression of foreign genes in yeast, it seems likely that the 5′-flanking sequences of any highly-expressed yeast gene could be used for the expression of important gene products. Any of the 3′-flanking sequences of these genes could also be used for proper termination and mRNA polyadenylation in such an expression system.

Many yeast promoters also contain transcriptional control as they may be turned off or on by variation in growth conditions. Some examples of such yeast promoters are the genes that produce the following proteins: Alcohol dehydrogenase II, isocytochrome-c, acid phosphatase, degradative enzymes associated with nitrogen-metabolism, glyceraldehyde-3-phosphate dehydrogenase, and enzymes responsible for maltose and galactose utilization. Such a control region would be very useful in controlling expression of protein product—especially when their production is toxic to yeast. It should also be possible to put the control region of one 5'-flanking sequence with a 5'-flanking sequence containing a promoter from a highly expressed gene. This would result in a hybrid promoter and should be possible since the control region and the prometer appear to be physically distinct DNA sequences.

3. Cell Culture Systems/Cell Culture Vectors

Propagation of vertebrate cells in culture (tissue culture) has become a regular procedure in recent years. The COS-7 line of monkey kidney fibroblasts may be employed as the host for the production of animal interferons (1). However, the experiments detailed here could be performed in any cell line which is capable of the replication and expression of a compatible vector, e.g., WI38, BHK, 3T3, CHO, VERO, and HeLa cell lines. Additionally, what is required of the expression vector is an origin of replication and a promoter located in front of the gene to be expressed, along with any necessary ribosome binding sites, RNA splice sites, polyadenylation site, and transcriptional terminator sequences. While these essential elements of SV40 have been exploited herein, it will be understood that the invention, although described herein in terms of a preferred embodiment, should not be construed as limited to these sequences. For example, the origin of replication of other viral (e.g., Polyoma, Adeno, VSV, BPV, and so forth) vectors could be used, as well as cellular origins of DNA replication which could function in a nonintegrated state.

B. Vector Systems

A useful vector to obtain expression consists of pBR322 sequences which provides a selectable marker for selection in *E. coli* (ampicillin resistance) as well as an *E. coli* origin of DNA replication. These sequences are derived from the plasmid pML-1 (2) and encompasses the region spanning the EcoRI and BamHI restriction sites. The SV40 origin is derived from a 342 base pair PVuII-HindIII fragment encompassing this region (both ends being converted to EcoRI ends). These sequences, in addition to comprising the viral origin of DNA replication, encode the promoter for both the early and late transcriptional unit. The orientation of the SV40 origin region is such that the promoter for the late transcriptional unit is positioned proximal to the gene encoding interferon.

DESCRIPTION OF THE DRAWINGS

FIGS. 2(*a* and *b*) shows the nucleotide sequences of two HGH genes and one HCS gene, with flanking regions. Nucleotide numbers refer to the HGH-N gene sequences, the first digit of any number appearing above the corresponding nucleotide. Positively numbered nucleotides start at the presumed cap site, and negatively numbered nucleotides are assigned to 5' flanking sequences. Negatively numbered triplets code for the respective signal peptides, positive numbers refers to the codons for the mature peptides. The TATAAA and AATAAA sequences diagnostic of eucaryotic structural genes are underlined. The human Alu family sequences in the 3' flanking region of the two HGH genes ae shown by lines above the nucleotides. The short region in the HCS gene homologous to one end of the Alu family sequences in the HGH genes is underlined.

FIG. 3 illustrates one HGH variant amino acid and nucleotide sequence. The primary structure of the protein was derived solely from the coding portion of the exons in the HGH-V gene (see FIG. 2). Differences in nucleotide sequence to the HGH-N gene and to the HGH protein sequence (3) are indicated below the variant sequences. Amino acid residue 9 in HGH can be proline or leucine as determined by cDNA sequencing (4).

DETAILED DESCRIPTION

Gene isolation and characterization

A human genomic library in bacteriophage λ (5) was screened for members of the human HGH gene family by in situ plaque hybridization (6) with cloned HGH cDNA sequences (4.7). This fragment was either 2.6, 2.9 or 9.5 kb in length as expected from a similar analysis of human genomic DNA (8). Hybridizing fragments were subcloned into the EcoRI site of plasmid pBR325 (9) and three (2.6, 2.6, and 2.9 kb) were chosen for a complete DNA sequence determination. The two smaller fragments originated from different phage isolates and had distinct restriction maps.

Figure 1:
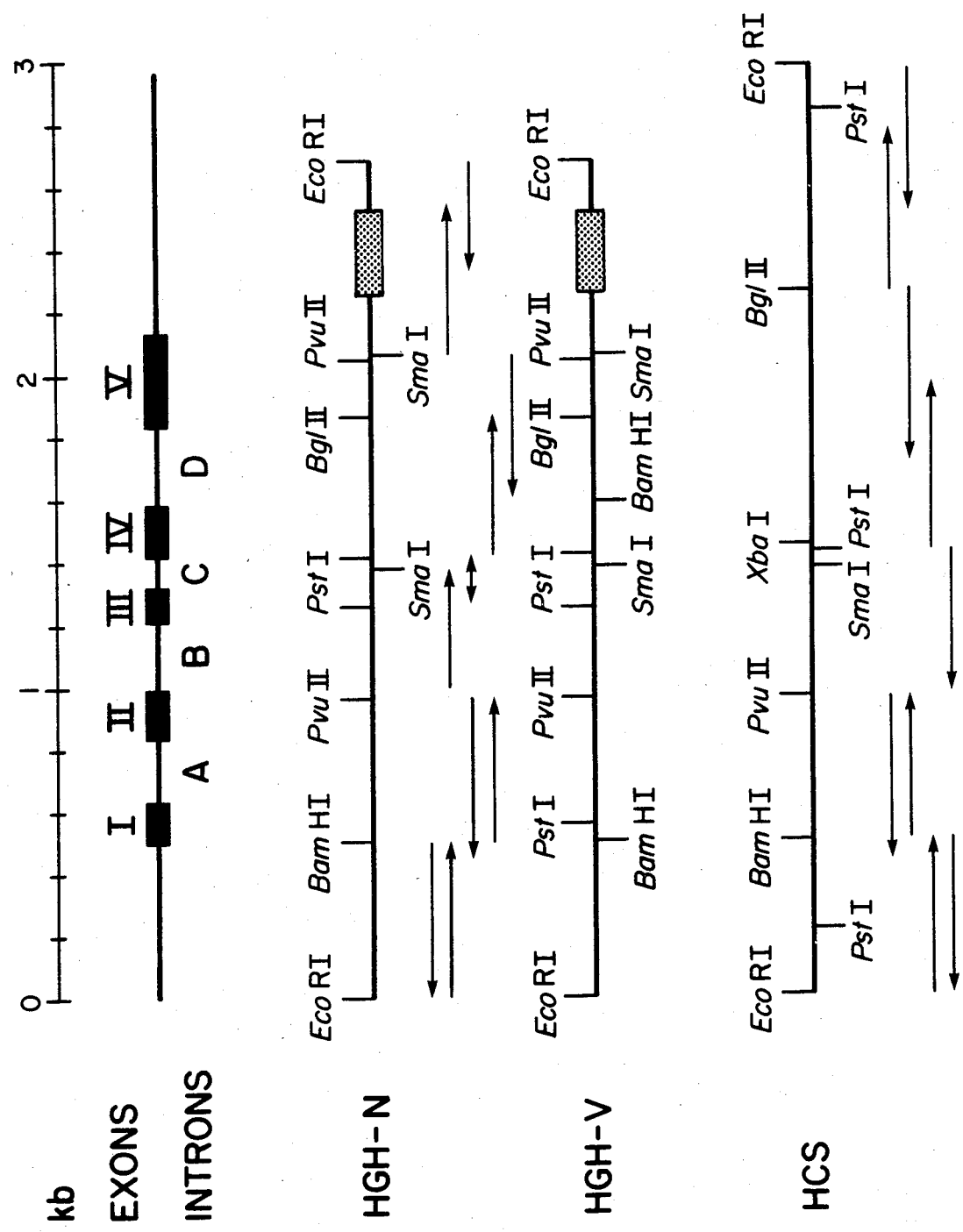
FIG. 1 depicts restriction maps and functional organization of three human genomic DNA fragments containing members of the HGH gene family.
Figure 4:
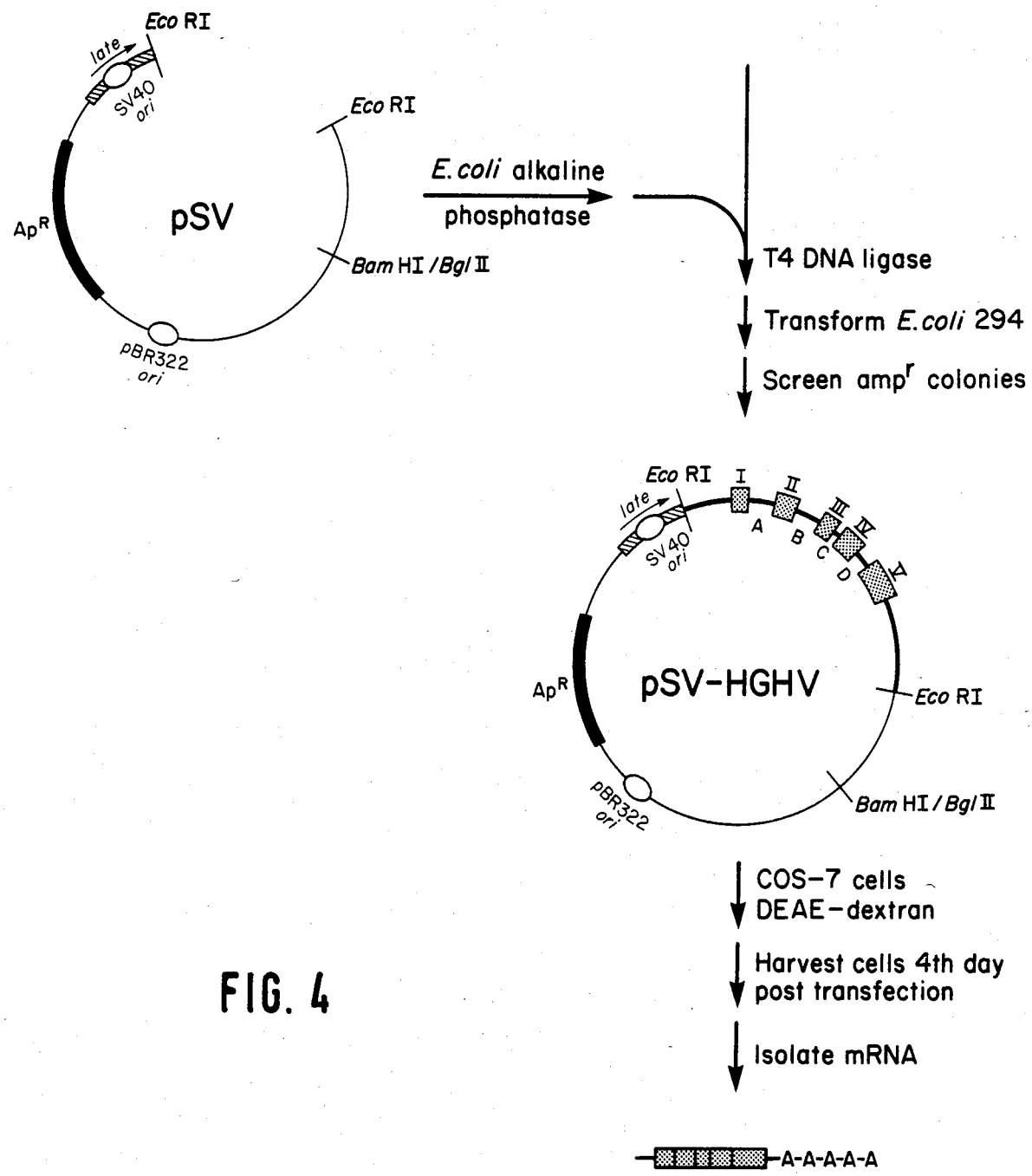
FIG. 4 illustrates a cell culture expression vector construction hereof, namely pSV-HGH-V, harboring the gene encoding a HGH variant protein hereof.

For sequence analysis the three genomic DNA fragments were excised from the plasmid DNA and isolated by polyacrylamide gel electrophoresis. Restriction maps for several specific endonucleases were obtained by standard methods and are shown in FIG. 1. Overlapping segments corresponding to defined restriction fragments were inserted into phage M13mp7 RF-DNA (10) and single-stranded recombinant phage DNAs were used as templates in enzymatic sequencing reactions (11) using a synthetic oligonucleotide as universal primer (10).

The complete nucleotide sequences of the three genomic DNA fragments aligned to one another and segmented into exons, introns, and nontranscribed (flanking) regions are shown in FIG. 2. Segmentation was achieved by comparison to the primary structures of HGH and HCS cDNA, and facilitated by the close homology of the three sequences. Whereas the entire nucleotide sequence of HGH mRNA (except for part of the 5'-untranslated region) is known (4,7) only a large part of the sequence of HCS and mRNA has been reported (12, 13).

The following description provides further detail enabling the practice of the invention.

Approximately 10⁶ recombinant λ4A phage carrying human chromosomal DNA were plated onto 20 150 mm petri dishes and screened (6) with radioactivity labeled cloned HGH cDNA (7) (specific activity $>10^8$ cpm/μg, approximately $10^6$ cpm per filter). The preparation of this probe was as described (8). Twelve phage were isolated, subjected to 2 rounds of screening for phage purification, grown in *E. coli* strain DP50supF (ATCC No. 39061, deposited Mar. 5, 82) and prepared from lysed cultures as described (14). Aliquots (1 μg) from each phage DNA were digested with endo EcoRI and Southern blots (15) of the digests were hybridized with the cloned HGH cDNA probe. Hybridizing fragments were either 9.5, 2.9 or 2.6 kb in size and were subcloned into the EcoRI site of plasmid pBR325 (9) using the same HGH probe in colony hybridizations (16) on chloramphenicol sensitive clones. Three subcloned EcoRI fragments 2.6, 2.6, and 2.9 kb long and containing two HGH genes and one HCS gene were subjected to a crude restriction analysis. Plasmid DNA was extracted from 1 l cultures amplified with chloramphenicol (200 μg/ml) during the log phase of growth. DNA extraction and purification by a cleared lysate technique was essentially as described (17). RNA was removed by digestion with RNAase (10 μg/ml) and chromatography on agarose A50 m. Plasmid DNAs were cut to completion with endo EcoRI and cloned DNA fragments isolated by excision from 6 percent polyacrylamide gels. To obtain maps gel-isolated DNA fragments were cleaved with one or more of the following restriction endonucleases (supplier BRL): BamHI, BglII, PvuII, PstI, SmaI, and XbaI. Typically, reactions were in 20 μl of 10 mM Tris.HCl, pH 7.5, 0.1 mM EDTA, 7 mM MgCl₂, 10 mM DTT, containing 500 mg of DNA and 2 U of enzyme, and were incubated for 1 hr at 37° C. Digests were separated on 6 or 8 percent polyacrylamide gels with parallel runs of plasmid pBR322 DNA cut with endo Hinf or NaeIII for size markers. DNA in gels was visualized by ethidium bromide staining and UV light.

The exact locations of the enzyme recognition sites shown above were obtained from the final DNA sequences (see FIG. 2). The location of exons was determined from comparisons to cloned cDNA sequences as described in the text. The stippled boxes in the 3' flanking regions of two HGH genes indicate the location of members of the human Alu family. Arrows show the strategy used for sequencing more than 95 percent of the three genomic DNA fragments. Overlaps were generated and sequences confirmed by sequencing selected gel-isolated restriction fragments.

The sequencing strategy indicated by the arrows in FIG. 1 yielded more than 95 percent of the DNA sequences shown above. Necessary overlaps were generated and unclear gel data resolved by sequencing selected gel-isolated sections. Plasmid-cloned and gel-isolated genomic EcoRI fragments (300 ng) were cleaved with one or two of the restriction endonucleases employed for mapping (see also arrows in FIG. 1). Reaction conditions were as described in the legend to FIG. 1, except that deoxyribonucleoside triphosphates (50 μM each) and E. coli DNA polymerase I large fragment (0.5 U, Boehrin or Mannheim) were added to generate blunt-ended DNA pieces for convenient insertion into a phage vector. Digested DNA was extracted with phenol/chloroform, precipitated with ethanol and ligated to HincII-cleaved phage M13mp7 RF-DNA (10). Ligation reactions (20 μl) contained 20 ng RF-DNA, 100 ng digested genomic DNA fragment and 2 U T4 DNA ligase (New England Biolabs) in 50 mM Tris.HCl, pH 8.0, 0.1 mM EDTA, 10 mM MgCl₂, 10 mM DTT, and 500 μM rATP. Reactions were incubated at room temperature for 4 hr and used to transform E. coli. Plating of transformation mixtures, plaque selection, phage growth and preparation of single-stranded DNA templates for sequencing were as described (10). To avoid redundancy templates were sorted by single track analysis (18) prior to complete sequencing. Selected DNA templates were sequenced by the dideoxynucleotide chain termination method (11) using a 15 nucleotide long synthetic primer (10).

Sequencing reactions (5 μl, 300 ng template DNA) were terminated by the addition of 10 μl of 98 percent deionized formamide, 10 mM EDTA, 0.2 percent bromophenol blue and 0.2 percent xylene cyanol. Terminated reaction mixtures were heated for 3 min. at 100° C. and 1 μl aliquots were electrophoresed on 40 cm long 5 percent polyacrylamide-8M urea "thin" gels (19) for 2 to 6 hr at 30 mA/1.8 kV. Gels were then transferred onto Whatman 3 MM paper, vacuum-dried, and exposed to Xray film for an average of 12 hrs.

Function and organization of sequences within genomic fragments

The functional organization of the highly homologous sequences within the three fragments is identical throughout the first 2,200 base pairs. Each fragment contains one gene intact with regard to all currently known sequence features (see below), and several hundred base pairs of non-transcribed sequences flanking the genes. Approximately 470 base pairs from the 5' end of each fragment is a TATAAA sequence characteristic of eukaryotic promoters (20). The beginning of exon I (cap site) was tentatively assigned to an A residue 30 nucleotides downstream of this regulatory sequence. This location of the cap site is in good agreement with that of many eukaryotic genes (21–25) and precedes the BamHI site present in all three fragments by one nucleotide. Each gene has the potential to code for a protein of 217 amino acids, the first 26 constituting a signal peptide. The coding sections are interrupted four times at identical locations by small introns, between 260 base pairs (intron A) and 90 base pairs (C) in size. All intervening sequences start with a GT dinucleotide, and end with an AG, analogous to other reported splice sequences (26).

The first exon (exon I) contains approximately 60 nucleotides of 5'-untranslated sequence, the first 3 codons of the signal peptide and the first nucleotide of the fourth codon. The second exon starts with the two remaining bases for the fourth codon and carries the rest of the coding region for the signal peptide together with 31 codons for the mature protein. The third exon consists of 40 triplets (for amino acids 32 to 71), the fourth exon of 55 (72 to 126) and the fifth of 65 (127–171). The last exon extends past the translational termination signal by approximately 100 nucleotides and features the AATAAA sequence common to most polyadenylated mRNAs (27), about 20 bases upstream of the presumed transcriptional termination site.

The 3'-flanking regions show close homology for about 100 nucleotides, at which point both 2.6 kb EcoRI fragments diverge in sequence from the 2.9 kb DNA. They contain a block of middle repetitive sequences (nucleotides 1732–2005) as evidenced by the intense smear on a Southern blot when these regions are used to probe restricted human DNA. Comparison to a consensus sequence (28) reveals that these sequences are 270 base pair long members of the human Alu family suggested to function as origins in DNA replication (29). The Alu family sequences are known to be transcribed by RNA polymerase III (30) and are inserted such that transcription would be from the opposite strand to that of the HGH genes. A detailed comparison of these regions with those similar in other human genes is presented elsewhere (31).

The remainder of the sequences on the 2.6 kb fragments have unknown function. The function of the sequences that constitute the last 700 nucleotides of the 2.9 kb fragment is also not shown. Probing human genomic DNA with these latter sequences shows that they occur in the 2.9 and 9.5 kb genomic EcoRI fragments but not in the 2.6 kb fragments. EcoRI fragments of all three size classes hybridize when the whole 2.9 kb DNA is used as a probe, indicating the absence of repetitive sequences in this DNA.

The genes and their products

All three non-allelic fragments contain functional genes as judged by the presence of promoters and polyadenylation signals, correct intron-exon junctions and by the absence of codon aberrations in exons (e.g. deletions, insertions, additional stop codons) which would lead to truncated translational products. In expressions, hnRNAs of approximately 1,650 bases are produced that can be processed to 800 nucleotide long mRNAs (not counting the 3'-polyA tail), containing 60 and 100 bases of 5'- and 3'-untranslated region respectively. The primary translation products of these mRNAs are proteins of 217 amino acids including an N-terminal signal sequence of 26 residues.

Figure 3:
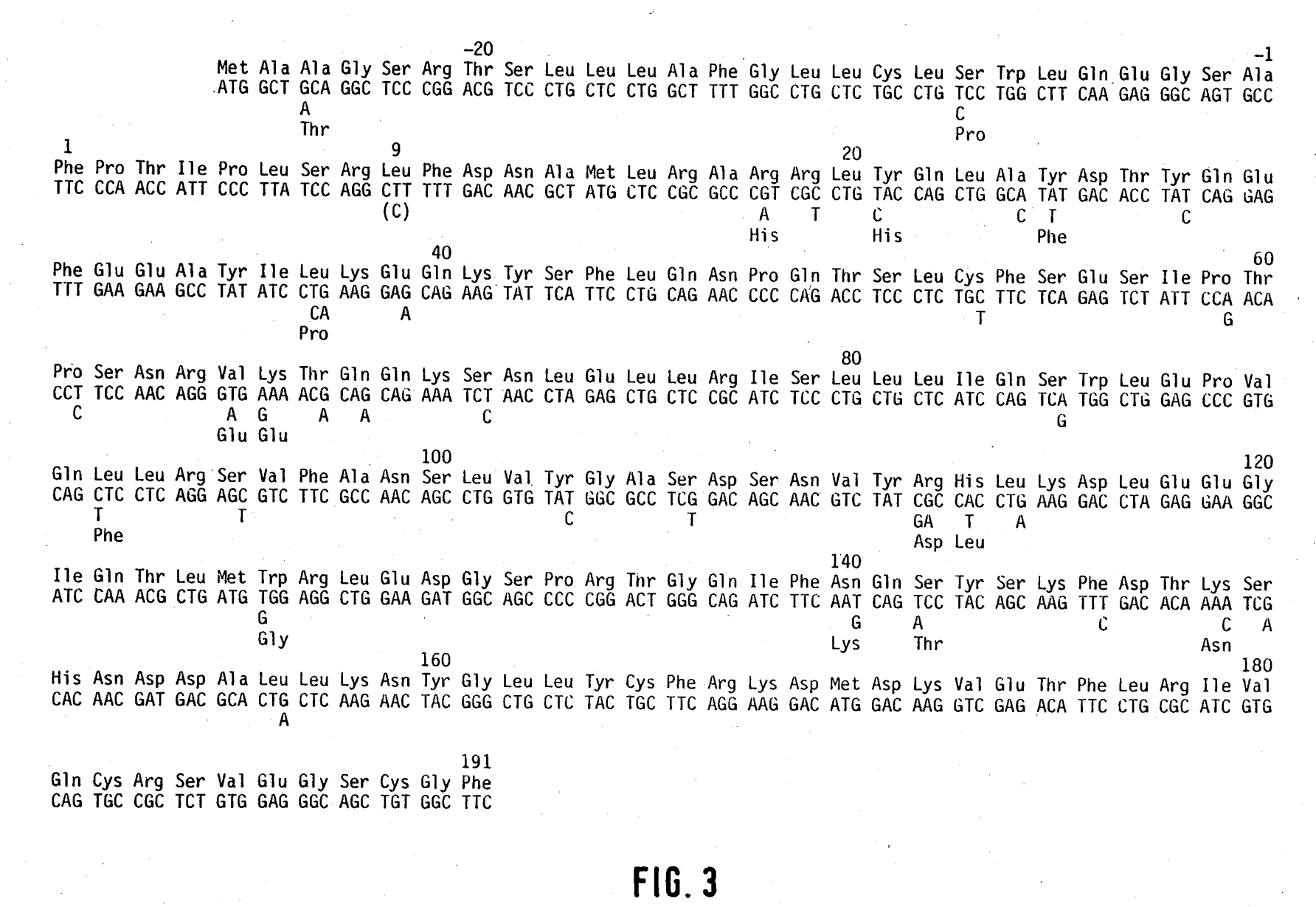

The fact that the exons contained on the first sequence in FIG. 2 are nucleotide for nucleotide the same as in cloned HGH cDNA (4,7) suggests that the corresponding genomic fragment contains the human growth hormone gene expressed in the pituitary to produce somatotropin. This contention is corroborated by the finding that no HGH is produced in individuals afflicted with a deletion in chromosome 17 which spans a 2.6 kb EcoRI fragment bearing identical map characteristics. The non-allelic EcoRI fragment containing two BamHI sites is not affected by this deletion and the presence of this gene cannot restore growth (32). As shown in FIG. 3, the protein product of this gene differs from preHGH by 15 amino acids. Two of the differences occur in the signal peptide and are conservative in nature. It is important to note that many of the amino acid changes in the mature part of the protein are non-conservative and are expected to change the properties of the protein considerably. Such changes occur at positions 18 (His→Arg), 21 (His→Tyr), 65 (Gln→Val), 66 (Glu→Lys), 112 (Asp→Arg), 113 (Leu→His), 126 (Gly→Trp), 140 (Lys→Asn), and 149 (Asn→Lys). Thus, this protein has lost two acidic amino acids and gained three basic ones over HGH leading to an increase in isoelectric point from 5.5 for HGH to 8.9 for the variant.

These changes result in a 20-fold lower cross-reactivity to HGH antibodies (33) and are expected to lead to a considerable increase in isoelectric point. Curiously, its receptor binding efficiency seems to be comparable to HGH (33) making the variant a possible competitive inhibitor of HGH action. The latter results were obtained by characterizing the protein produced from the variant gene employing an SV40 expression system. Although transcription of the gene was controlled primarily by a viral promoter (33), the fact that the 5'-flanking sequences of both the HGH-V and the HGH-N gene contain a functional promoter (34) strongly suggest that the HGH-V gene is a functional gene expressed in vivo.

It is not known whether the variant protein is actually produced in vivo and if so, in which tissue. Although the pituitary is a probable production site for the protein one should bear in mind that the known tissue specificity of HGH and HCS gene expression could hold for other members of the HGH gene family which may be synthesized elsewhere in the body.

Different from HGH and HCS, and also from all the known animal growth hormones (35), the HGH variant features a second tryptophan residue. In addition to the amino acid changes 17 nucleotide differences result in synonymous codons and 2 and 4 changes occur in the 5' and 3' untranslated regions respectively.

It is of interest to point out that the HGH-V gene may also code for a protein by 15 residues smaller than the 191 amino acid long product described above. This is in formal analogy to the biosynthesis of HGH where approximately 10 percent of the pituitary-produced hormone consists of a shorter version of HGH ("20K variant") which is missing amino acid residues 31–45 (36). The hypothesis that HGH and its deletion variant are generated by different splicing events of the same primary transcript was proposed by Wallis (37), and recent data seem to substantiate this motion (25). The coding sequences for residues 31 to 45 constitute the beginning of exon III and are identical in the HGH-N and HGH-V genes. Since both sequences carry a canonical splice site (nucleotides 730–745, see FIG. 2), the primary transcript of the HGH-V gene could be spliced inside of exon III resulting in a shorter mRNA similar to the one which codes for the HGH deletion variant. Although the HGH-V gene has not been documented to be expressed in vivo, its intact nature, its chromosomal location within that of the HGH gene family and the fact that it can be expressed in vitro (33) suggest that it is functional.

Possible regulatory sequences

The expression of the HGH gene is controlled by glucocorticoids and thyroid hormones. In cultured rat pituitary cells both types of hormones have a synergistic effect on the production of rat GH and its mRNA (38,39). Such hormone action is mediated by receptor proteins which are thought to interact with specific DNA sequences located in the vicinity of responsive genes (38,39). Recently, hormonally responsive transcription of the HGH-N gene and HGH synthesis could be demonstrated in murine fibroblasts transformed with the respective human genomic 2.6 kb EcoRI fragment (34). The sequencees involved in the hormonal induction are contained within 500 base pairs of 5'-flanking region as shown by fusing the corresponding section from the 2.6 kb DNA to the thymidine kinase gene and thereby rendering this gene responsive to dexamethasone (34).

According to current models this region provides sequence elements for the specific binding of glucocorticoid receptor-hormone complex(es) (40). Although such specific interaction could be demonstrated with MMTV DNA and purified receptor protein (41) the respective binding site(s) has not yet been analyzed, leaving the nature of relevant sequences open to speculation. Thus, any of the prominent features that occur in the 5'-flanking sequence of the HGH-N gene could play a role in receptor recognition. These features consist of purine rich nucleotide stretches and palindromic structures.

The Goldstein-Hogness box, for example, lies near the end of a stretch of 62 nucleotides (−81 to −20, FIG. 2) of which only 14 are pyrimidines. Such an uneven distribution of purines and pyrimidines can cause helix destabilization and may facilitate the local melting of DNA strands possibly involved in hormone-mediated transcriptional induction. This region spans the location of the CAT box found in other genes (21), but no good fit with a consensus sequence is detectable at an appropriate distance from the TATA box. Since the sequence in this position is thought to be involved in the rate of transcriptional initiation (42,43) lack of homology to other systems may reflect a special type of transcriptional regulation of the HGH-N gene.

An extended region with palindromes and inverted repeats is found between nucleotides −304 and −198. Towards the middle lie two imperfect inverted repeat sequences of 15 (−278 to −264) and 17 base pairs (−238 to −222) which are separated by 25 base pairs containing a section very rich in purines. Each inverted repeat is composed of two parts, 6 and 7 bases long with perfect homologies in their counterparts, but separated in one repeat by 2 nucleotides and in the other by 4. Three palindromes occur in the vicinity (−290 to −285, −265 and −260, and −213 to −205) and two of them overlap with 15 nucleotides long imperfect inverted repeats (−304 to −290, and −198 to −212) located at the beginning and end of the whole region.

Approximately 80 base pairs upstream is another highly purine-rich sequence (−371 to −358) where 31 out of 34 nucleotides are purines. In the middle of this region one finds a repeat of the sequence GGATAG of which a single copy is found in the complementary strand 38 base pairs downstream (−321 to −328). Sequence elements that display dyed symmetry such as palindromic structures and inverted repeats are possible candidates for interaction with hormone receptors, since such DNA structures are known to be involved in the regulation of procaryotic gene expression (44).

It is worth noting that purine-rich regions are also found in the introns of the HGH gene, and that some of them show homology to small regions of other hormone-responsive sequences (e.g. MMTV (45), rat GH gene (24) and mouse metallothionine gene (22)). Whether such homology is fortuitous, or related to hormone-responsive gene expression remains to be elucidated.

Expression of gene in cell culture

The following description defines the means and methods for isolating HGH-V mRNA via an expression vector, pSV-HGH-V. The 342 base pair HindIII-PvuII fragment encompassing the SV40 origin was converted to an EcoRI restriction site bound fragment. The HindIII site was converted by the addition of a synthetic oligomer (5'dAGCTGAATTC) and the PvuII site was converted by blunt-end ligation into an EcoRI site filled in using Polymerase I (Klenow fragment). The resulting EcoRI fragment was inserted into the EcoRI site of pML-1 (2). A plasmid with the SV40 late promoter oriented away from the $amp^R$ gene was further modified by removing the EcoRI site nearest the $amp^R$ gene of pML-1 (46).

The 1023 base pair HpaI-BglII fragment of cloned HBV DNA (47) was isolated and the HpaI site of hepatitis B virus (HBV) converted to an EcoRI site with a synthetic oligomer (5'dGCGAATTCGC). This EcoRI-BglII bounded fragment was directly cloned into the EcoRI-BamHI sites of the plasmid described above carrying the origin of SV40.

Into the remaining EcoRI site was inserted the HGH-V gene on a 1250 base pair PstI fragment of p69 after conversion of the PstI ends to EcoRI ends. Clones were isolated in which the SV40 late promoter preceded the structural gene of HGH-V. The resulting plasmids were then introduced into tissue culture cells (Gluzman et al., Cold Spring Harbor Sym. Quant. Biol. 44, 293 (1980)) using a DEAE-dextran technique (48) modified such that the transfection in the presence of DEAE-dextran was carried out for 8 hours. Cell media was changed every 2-3 days. 200 microliters was removed daily for bioassay. Typical yields were 300-500 ng/ml on samples assayed three or four days after transfection.

DNA encoding human growth hormone variants can be constructed for use in expression of protein in cell culture by using chemically synthesized DNA in conjunction with enzymatically synthesized DNA. The hybrid DNA, encoding heterologous polypeptide is provided in substantial portion, preferably a majority, via reverse transcription of mRNA while the remainder is provided via chemical synthesis. In a preferred embodiment, synthetic DNA encoding the first 24 amino acids of human growth hormone variant (HGH-V) is constructed according to a plan which incorporates an endonuclease restriction site in the DNA corresponding to HGH-V amino acids 23 and 24. This is done to facilitate a connection with downstream HGH-V cDNA sequences. The various oligonucleotide fragments making up the synthetic part of the DNA are chosen following known criteria for gene synthesis: avoidance of undue complementarity of the fragments, one with another, except, of course, those destined to occupy opposing sections of the double stranded sequence; avoidance of AT rich regions to minimize transcription termination; and choice of microbially preferred codons. Following synthesis, the fragments are permitted to effect complementary hydrogen bonding and are ligated according to methods known per se.

The greater portion of the DNA coding sequence can be provided as described above from genomic DNA. This portion encodes the C-terminal of the polypeptide and is ligated, in accordance herewith, to the remainder of the coding sequence, obtained by chemical synthesis, optionally including properly positioned translational start and stop signals and upstream DNA through the ribosome binding site and the first nucleotide (+1) of the resultant messenger RNA. The synthetic fragment can be designed by nucleotide choice dependent on conformation of the corresponding messenger RNA in order to avoid secondary structure imposed limitations on translation.

REFERENCES

1. Gluzman, Cell 23, 175 (1981).
2. Lusky et al., Nature 293, 79 (1981).
3. Li, C. H. Proc. Am. phil. Soc. 116, 365 (1972).
4. Roskam, W. G. and Rougeon, F. Nuclei Acids Res. 7, 305-320, 1979.
5. Lawn, R. H., Fritsch, E. F., Parker, R. C., Blake, G. and Maniatis, T. Cell 15, 1157-1174 (1978).
6. Benton, W. D. and Davis, R. W. Science 196, 180-182 (1977).
7. Goodman, H. M. et al. in Specific Eukaryotic Genes, eds. Engberg, J., Klenow, H. and Leick, V. (Munskagaard, Copenhagen), pp. 179-190 (1979).
8. Fiddes, J. C. et al. Proc. natn. Acad. Sci. U.S.A. 76, 4294-4298 (1979).
9. Bolivar, F. Gene 4, 121-136 (1978).
10. Messing, J., Crea, R. and Seeburg, P. H. Nucleic Acids Res. 9, 309-321 (1981).
11. Sanger, F., Nicklen, S. and Coulson, A. R. Proc. natn. Acad. Sci. U.S.A. 74, 5463-5467 (1977).
12. Seeburg, P. H. et al. Cell 12, 157-165 (1977).

13. Shine, J., Seeburg, P. H., Martial, J. A., Baxter, J. D. and Goodman, H. M. *Nature* 270, 494–499 (1977).
14. Blattner et al., *Science* 202, 1279 (1978).
15. Southern, E. M. *J. Mol. Biol.* 98, 503–517 (1975).
16. Grunstein, M. and Hogness, D. S. *Proc. natn. Acad. Sci. U.S.A.* 72, 3961–3965 (1975).
17. Betlach, M. C. et al. *Fed. Proc.* 35, 2037–2043 (1976).
18. Sanger, F., Coulson, A. R., Barrell, B. G., Smith, A. J. H. and Roe, B. A. *J. mol. Biol.* 143, 161–178 (1980).
19. Sanger, F. and Coulson, A. R. *FEBS Lett.* 87, 107–110 (1980).
20. Goldberg, M. (1979) Ph.D. thesis, Stanford University, Stanford, Calif. U.S.A.
21. Benoist, C., O'Hara, K., Breathnach, R. and Chambon, P. *Nucleic Acids Res.* 8, 127–142 (1980).
22. Glanville, N., Durnam, D. M. and Palmiter, R. D. *Nature* 292, 267–269 (1981).
23. Corden, J. et al. *Science* 209, 1406–1414 (1980).
24. Barta, A., Richards, R., Baxter, J. D. and Shine, J. *Proc. natn. Acad. Sci. U.S.A.* 78, 4867–4871 (1981).
25. DeNoto, F. M., Moore, D. D. and Goodman, H. M. *Nucleic Acids Res.* 9, 3719–3730 (1981).
26. Breathnach, R. et al., *Proc. natn. Acad. Sci.* 75, 4853–4857 (1978).
27. Proudfoot, N. J. and Brownlee, G. G. *Nature* 263, 211–214 (1976).
28. Deininger, P. L., Jolly, D. J., Rubin, C. M., Friedmann, T. and Schmid, C. W. *J. mol. Biol.* 151, 17–35 (1981).
29. Jelinek, W. R. et al. *Proc. natn. Acad. Sci. U.S.A.* 77, 1398–1402 (1980).
30. Pan, J., Elder, J. T., Duncan, C. H. and Weissman, S. M. *Nucleic Acids Res.* 9, 1151–1170 (1981).
31. Houck, C., Seeburg, P. H., Najarian, R., Franke, A. and Lawn, R. submitted to *Nucleic Acids Res.* (1982).
32. Phillips, J. A. III, Hjelle, B. L., Seeburg, P. H. and Zachmann, M. *Proc. natn. Acad. Sci. U.S.A.* 78, 6372–6375 (1981).
33. Pavlakis, G. N., Hizuka, N., Gorden, P., Seeburg, P. H. and Hamer, D. H. *Proc. natn. Acad. Sci. U.S.A.* 78, 7398–7402 (1981).
34. Robins, D. M., Pack, I., Seeburg, P. H. and Axel, R. *Gene*, in the press.
35. Dayhoff, M. O. in Atlas of Protein Sequence and Structure (Natl. Biomedical Res. Foundation, Georgetown University Medical Center, Washington, D.C.) Vol. 5, Suppl. 2, p. 123 (1976).
36. Lewis et al., *Biochem. Biophys. Res. Comm.* 92, 511 (1980).
37. Wallis, M. *Nature* 284, 512 (1980).
38. Martial, J. A., Baxter, J. D., Goodman, H. M. and Seeburg, P. H. *Proc. natn. Acad. Sci.* 74, 1816–1820 (1977).
39. Martial, J. A., Seeburg, P. H., Guenzi, D., Goodman, H. M. and Baxter, J. D. *Proc. natn. Acad. Sci. U.S.A.* 74, 4293–4295 (1977).
40. Yamamoto, K. R. and Alberts, B. M. *Annual Rev. Biochem.* 45, 721–746 (1976).
41. Payvar, F. et al. *Proc. natn. Acad. Sci. U.S.A.* 78, 6628–6632 (1981).
42. Grosschedl, R. and Birnstiel, M. L. *Proc. natn. Acad. Sci. U.S.A.* 77, 1432–1436 (1980).
43. McKnight, S. L., Gavis, E. R., Kingsbury, R. and Axel, R. *Cell* 25, 385–398 (1981).
44. Gilbert, W. and Maxam, A. *Proc. natn. Acad. Sci. U.S.A.* 70, 3581–3585 (1973).
45. Donehower, L. A., Huang, A. L. and Hager, G. L. *J. Virology* 37, 226–238 (1981).
46. Itakura et al., *Science* 198, 1056 (1977).
47. Valenzuela et al., Animal Virus Genetics (Ed. Fields et al.) Academic Press, NY (1980), p. 57.
48. McCuthan et al., *J. Natl. Amer. Inst.* 41, 351 (1968).

I claim:

1. A replicable cloning vehicle comprising an inserted DNA sequence, said inserted DNA sequence encoding a human growth hormone variant protein having the amino acid sequence phe pro thr ile pro leu ser arg leu phe asp asn ala met leu arg ala arg arg leu tyr gln leu ala tyr asp thr tyr gln glu phe glu glu ala tyr ile leu lys glu gln lys tyr ser phe leu gln asn pro gln thr ser leu cys phe ser glu ser ile pro thr pro ser asn arg val lys thr gln gln lys ser asn leu glu leu leu arg ile ser leu leu leu ile gln ser trp leu glu pro val gln leu leu arg ser val phe ala asn ser leu val tyr gly ala ser asp ser asn val tyr arg his leu lys asp leu glu glu gly ile gln thr leu met trp arg leu glu asp gly ser pro arg thr gly gln ile phe asn gln ser tyr ser lys phe asp thr lys ser his asn asp asp ala leu leu lys asn tyr gly leu leu tyr cys phe arg lys asp met asp lys val glu thr phe leu arg ile val gln cys arg ser val glu gly ser cys gly phe.

2. A DNA isolate consisting essentially of the inserted DNA sequence of claim 1.

3. An expression vector comprising an inserted DNA sequence, said inserted DNA sequence encoding a human growth hormone variant protein having the amino acid sequence phe pro thr ile pro leu ser arg leu phe asp asn ala met leu arg ala arg arg leu tyr gln leu ala tyr asp thr tyr gln glu phe glu glu ala tyr ile leu lys glu gln lys tyr ser phe leu gln asn pro gln thr ser leu cys phe ser glu ser ile pro thr pro ser asn arg val lys thr gln gln lys ser asn leu glu leu leu arg ile ser leu leu leu ile gln ser trp leu glu pro val gln leu leu arg ser val phe ala asn ser leu val tyr gly ala ser asp ser asn val tyr arg his leu lys asp leu glu glu gly ile gln thr leu met trp arg leu glu asp gly ser pro arg thr gly gln ile phe asn gln ser tyr ser lys phe asp thr lys ser his asn asp asp ala leu leu lys asn tyr gly leu leu tyr cys phe arg lys asp met asp lys val glu thr phe leu arg ile val gln cys arg ser val glu gly ser cys gly phe, operably linked to an expression effecting DNA sequence and flanked by translational start and stop signals.

4. A viable cell culture comprising cells transformed with the expression vector of claim 3.

5. A DNA isolate consisting essentially of a DNA sequence encoding an amino-terminal presequence-containing human growth hormone variant protein of the amino acid sequence met ala ala gly ser arg thr ser leu leu leu ala phe gly leu leu cys leu ser trp leu gln leu gly ser ala phe pro thr ile pro leu ser arg leu phe asp asn ala met leu arg ala arg arg leu tyr gln leu ala tyr asp thr tyr gln glu phe glu glu ala tyr ile leu lys glu gln lys tyr ser phe leu gln asn pro gln thr ser leu cys phe ser glu ser ile pro thr pro ser asn arg val lys thr gln gln lys ser asn leu glu leu leu arg ile ser leu leu ile gln ser trp leu glu pro val gln leu leu arg ser val phe ala asn ser leu val tyr gly ala ser asp ser asn val tyr arg his leu lys asp leu glu glu gly ile gln thr leu met trp arg leu glu asp gly ser pro arg thr gly gln ile phe asn gln ser tyr ser lys phe asp thr lye ser his asn asp asp ala leu leu lys asn tyr gly leu leu tyr cye phe arg lys asp met asp lys val glu thr phe leu arg ile val gln cys arg ser val glu gly ser cys gly phe.

* * * * *